United States Patent

Coombes et al.

[11] Patent Number: 6,120,457
[45] Date of Patent: Sep. 19, 2000

[54] IN VIVO ZEROING OF CATHETER PRESSURE SENSOR

[75] Inventors: Alan Coombes, Hingham; Eric J. Brown, Stoughton, both of Mass.

[73] Assignee: Johnson & Johnson Professional, Inc., Raynham, Mass.

[21] Appl. No.: 08/887,481

[22] Filed: Jul. 2, 1997

[51] Int. Cl.[7] ..................................... A61B 5/02
[52] U.S. Cl. ........................... 600/486; 600/488; 600/561
[58] Field of Search ..................................... 600/486, 488, 600/561, 485; 73/4 R

[56] References Cited

U.S. PATENT DOCUMENTS

| | | | |
|---|---|---|---|
| 3,724,274 | 4/1973 | Millar | 73/398 AR |
| 3,748,623 | 7/1973 | Millar | 338/4 |
| 4,206,761 | 6/1980 | Cosman | 128/660 |
| 4,206,762 | 6/1980 | Cosman | 128/660 |
| 4,281,666 | 8/1981 | Cosman | 128/748 |
| 4,281,667 | 8/1981 | Cosman | 128/748 |
| 4,589,287 | 5/1986 | Dickens | 73/727 |
| 4,653,508 | 3/1987 | Cosman | 128/748 |
| 4,660,568 | 4/1987 | Cosman | 128/748 |
| 4,672,974 | 6/1987 | Lee | 600/561 |
| 4,901,735 | 2/1990 | Von Berg | 128/748 |
| 5,133,358 | 7/1992 | Gustafson et al. | 128/675 |
| 5,191,898 | 3/1993 | Millar | 128/748 |
| 5,203,340 | 4/1993 | Gustafson et al. | 128/675 |
| 5,257,630 | 11/1993 | Broitman et al. | 128/675 |
| 5,325,865 | 7/1994 | Beckman et al. | 128/748 |
| 5,460,183 | 10/1995 | Raynes et al. | 128/673 |
| 5,566,680 | 10/1996 | Urion et al. | 128/778 |
| 5,788,642 | 8/1998 | Hamatake et al. | 600/561 |

FOREIGN PATENT DOCUMENTS

0749721  12/1996  European Pat. Off. ...... A61B 5/0215

*Primary Examiner*—Max Hindenburg
*Assistant Examiner*—Ryan Carter
*Attorney, Agent, or Firm*—Nutter, McClennen & Fish LLP

[57] ABSTRACT

A catheter-based physiological pressure sensing device, which can be calibrated in vivo, is disposed in the distal end of a catheter, and is preferably in the form of a bulb-like device. The pressure sensing device includes a pressure sensor tip and pressure sensor element disposed in the pressure sensor tip. The pressure sensor element has first and second opposing surfaces which form separate and isolatable first and second chambers. An aperture is formed in an external wall of the pressure sensor tip to provide a passageway into the first chamber and expose the first surface of the pressure sensor element to a physiological pressure. A blocking element, such as a balloon, is disposed in the first chamber and is adapted for selectively blocking the aperture. To measure a physiological pressure, the aperture is unblocked to allow an outside pressure into the first chamber and a reference pressure is presented to the second chamber so that the surfaces of the pressure sensing element can measure the differential pressure. To calibrate or zero the device, the blocking element blocks the aperture to seal the first chamber with respect to external pressure and a fluid at a known pressure is introduced to the first and second chambers. The pressure sensor element provides an output signal indicative of a zero offset pressure to a pressure monitoring circuit to calibrate, or zero, the sensor and enhance the accuracy of subsequent pressure measurements.

11 Claims, 6 Drawing Sheets

IN VIVO ZEROING OF CATHETER PRESSURE SENSOR

CROSS REFERENCE TO RELATED APPLICATIONS

Not Applicable.

STATEMENTS REGARDING FEDERALLY SPONSORED RESEARCH

Not Applicable.

BACKGROUND OF THE INVENTION

Catheters are used in various medical applications, including the diagnosis, treatment and monitoring of medical conditions. One type of catheter includes a sensor for in vivo measurement of various physiological pressures. An illustrative application for a catheter-based pressure sensor is in the measurement of intracranial pressure in which one end of the catheter is disposed in the ventricular region of the brain and the other end exits the cranial region for coupling to a monitor.

Typical catheter pressure sensors utilize a pressure sensitive device, which may be capacitive, resistive, optical or ultrasonic. Generally, one side, or surface of the sensor is exposed to the physiological pressure to be measured and another surface of the sensor (i.e., the reference surface) is exposed to a liquid or gas at a reference pressure. The measured pressure differential between the sensor surfaces provides an indication of the physiological pressure to which the first surface is exposed.

As with most electronic sensing devices, it is advantageous to calibrate the catheter pressure sensor periodically to compensate for sensor drift at a zero pressure condition. Certain medical conditions result in an increase in intracranial pressure (e.g., due to production of excess cerebrospinal fluid). Pressures beyond a certain threshold can cause patient death or irreversible brain damage. It is thus necessary to obtain reliable pressure readings.

Calibration is typically achieved by applying a known, equal pressure to both surfaces of the sensor and measuring an output signal of the pressure sensor. The measured output signal represents a zero offset of the sensor and the process of calibration is thus sometimes referred to as "zeroing." Often, the known pressure at which the sensor is calibrated is atmospheric pressure. The measured zero offset of the sensor is used by a circuit to adjust the measured signal in order to compensate for the zero offset, thereby enhancing the pressure sensing accuracy of the device.

Some catheter pressure sensors permit calibration to be performed in vivo. One such catheter is described in U.S. Pat. No. 4,901,735 (von Berg) in which a balloon structure surrounds the entire catheter tip, where the sensor is located, and is inflated when calibration is performed. With the balloon inflated, a uniform pressure is exerted on both surfaces of a strain gauge sensor. Another catheter pressure sensor permitting in vivo zeroing is described in U.S. Pat. No. 5,203,340 (Gustafson et al.) in which an ex vivo pressure connecting means is provided for inhibiting liquid communication with the reference surface of the sensor and permitting the physiological pressure to be applied to both surfaces of the sensor. Although some pressure monitors are able to achieve in vivo zeroing, more reliable and effective calibration of in vivo monitors would be desirable.

SUMMARY OF THE INVENTION

The present invention relates to sensors for measuring pressures, and more particularly to a physiological pressure sensing device, implantable within a patient, that can be calibrated or zeroed in vivo. While the invention is applicable to a variety of pressure sensors of which calibration is desirable, the invention is described herein with respect to a catheter-based pressure sensing device.

The invention comprises a catheter-based physiological pressure sensing device that can be formed within a catheter. The pressure sensing device is preferably in the form of a bulb-like device that is formed within a catheter, such as at a distal end of the catheter. The pressure sensing device includes a pressure sensor tip having an external wall and an aperture disposed in the external wall for providing a passageway between the outside and inside of the catheter. A pressure sensor element is disposed within the pressure sensor tip with a first surface that is exposed to the aperture and an opposed second surface that is isolated from the aperture. The pressure sensor element separates the bulb-like device into separate and isolatable chambers.

A blocking element, such as a balloon, is disposed in a first chamber that is defined by the first surface of the pressure sensor element and a wall of the device that includes the aperture. The blocking element is adapted for selectively blocking the aperture. In a first position or condition, the blocking element occludes the aperture to effectively seal the first chamber with respect to the exterior of the catheter. When the blocking element is in a second condition, the first surface of the pressure sensor element is exposed to an external or physiological pressure via the aperture.

To measure a pressure, the blocking element is manipulated to the second condition, exposing the first surface of the pressure sensor element to an outside pressure, and a reference pressure is presented to the second chamber. The differential pressure between the first and second chambers is measured by the pressure sensor element which provides an output signal indicative of the differential pressure. The output signal preferably is delivered to an electrical conductor in electrical communication with a pressure monitoring circuit. The pressure monitoring circuit can display, record or otherwise indicate to a physician, or other medical personnel, the measured differential pressure.

To calibrate or zero the device, the balloon is inflated to block the aperture in the pressure sensor tip and seal the first chamber with respect to external pressure. A fluid at a known pressure, such as air at atmospheric pressure, is introduced to the first chamber. The same or a different fluid is then introduced into the second chamber at the same pressure as the first chamber. The pressure sensor element provides an output signal indicative of a zero offset pressure. This zero offset pressure is used by the pressure monitoring circuit to calibrate the sensor and enhance the accuracy of subsequent physiological pressure measurements.

BRIEF DESCRIPTION OF THE DRAWINGS

The invention will be more fully understood from the following detailed description taken in conjunction with the following drawings, in which.

DESCRIPTION OF THE PREFERRED EMBODIMENTS

Figure 1:
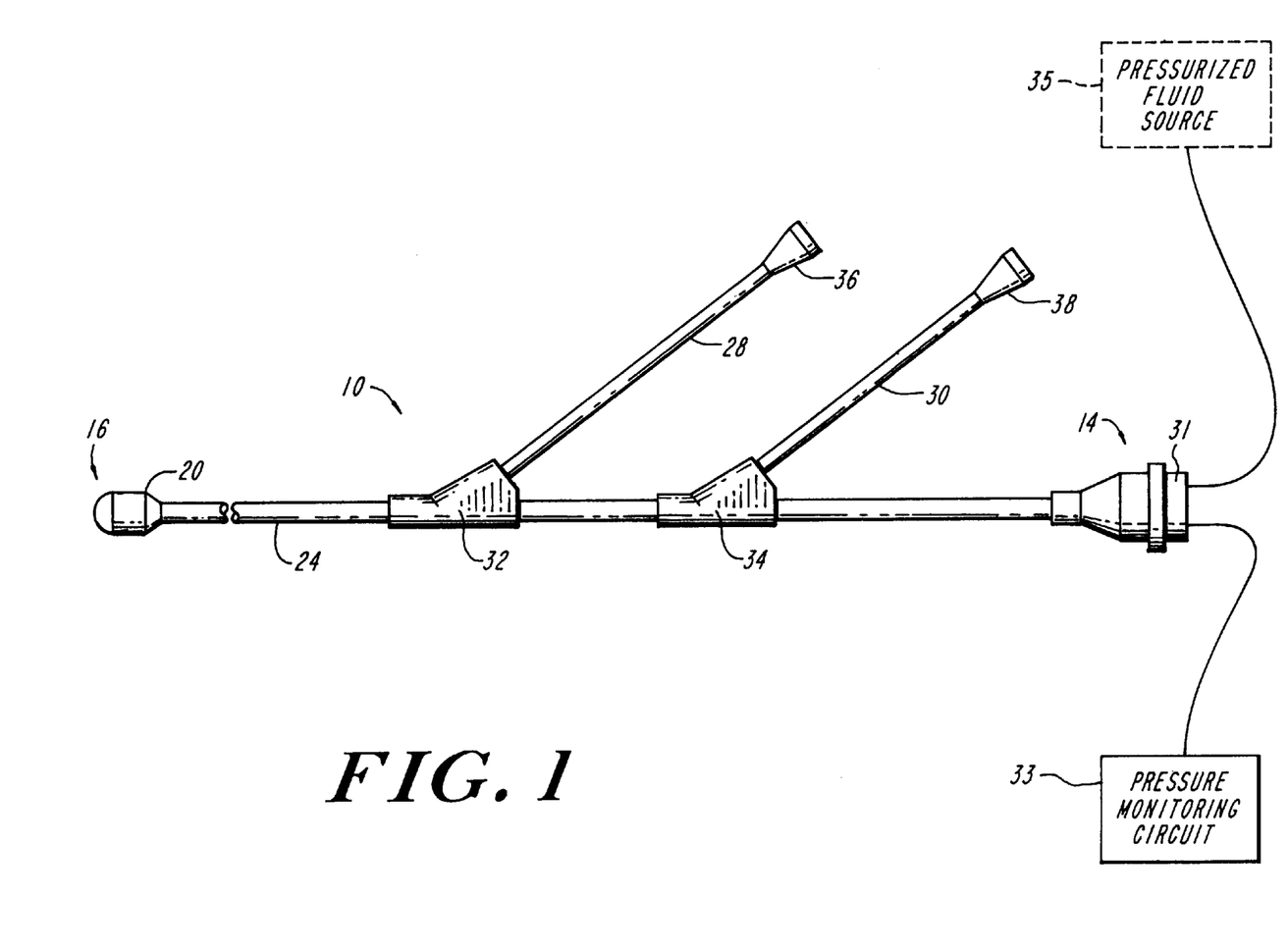
FIG. 1 shows a catheter having a pressure sensing device according to the invention disposed on its distal end.

Referring to FIG. 1, a catheter 10 is shown to have a proximal end 14 and a distal end 16. The distal end 16 includes a tip region 20 and is adapted for being inserted into a patient for performing an in vivo physiological pressure measurement, such as the monitoring of intracranial pressure.

The catheter 10 includes a flexible catheter tube 24 that forms a portion of passageways that extend between the proximal end 14 and the distal end 16 and a plurality of branch tubes 28, 30. The catheter tube 24 carries smaller tubes and electrical wires for connection to a pressure sensor device disposed in the tip region 20, as will be described in conjunction with FIG. 2. A connector 31 disposed at the proximal end 14 of the catheter is adapted for coupling to a pressure monitoring circuit 33. An optional pressurized fluid source 35 can also be coupled to the connector 31 for providing a fluid, such as air, to the tip region 20 at a predetermined pressure.

The branch tubes 28, 30 are coupled to the catheter tube 24 via respective Y-connectors 32, 34 and permit infusion or extraction of a liquid or gas from the tip region 20. To this end, each of the branch tubes 28, 30 includes a respective coupling 36, 38, such as a syringe or fluid coupling.

Figure 2:
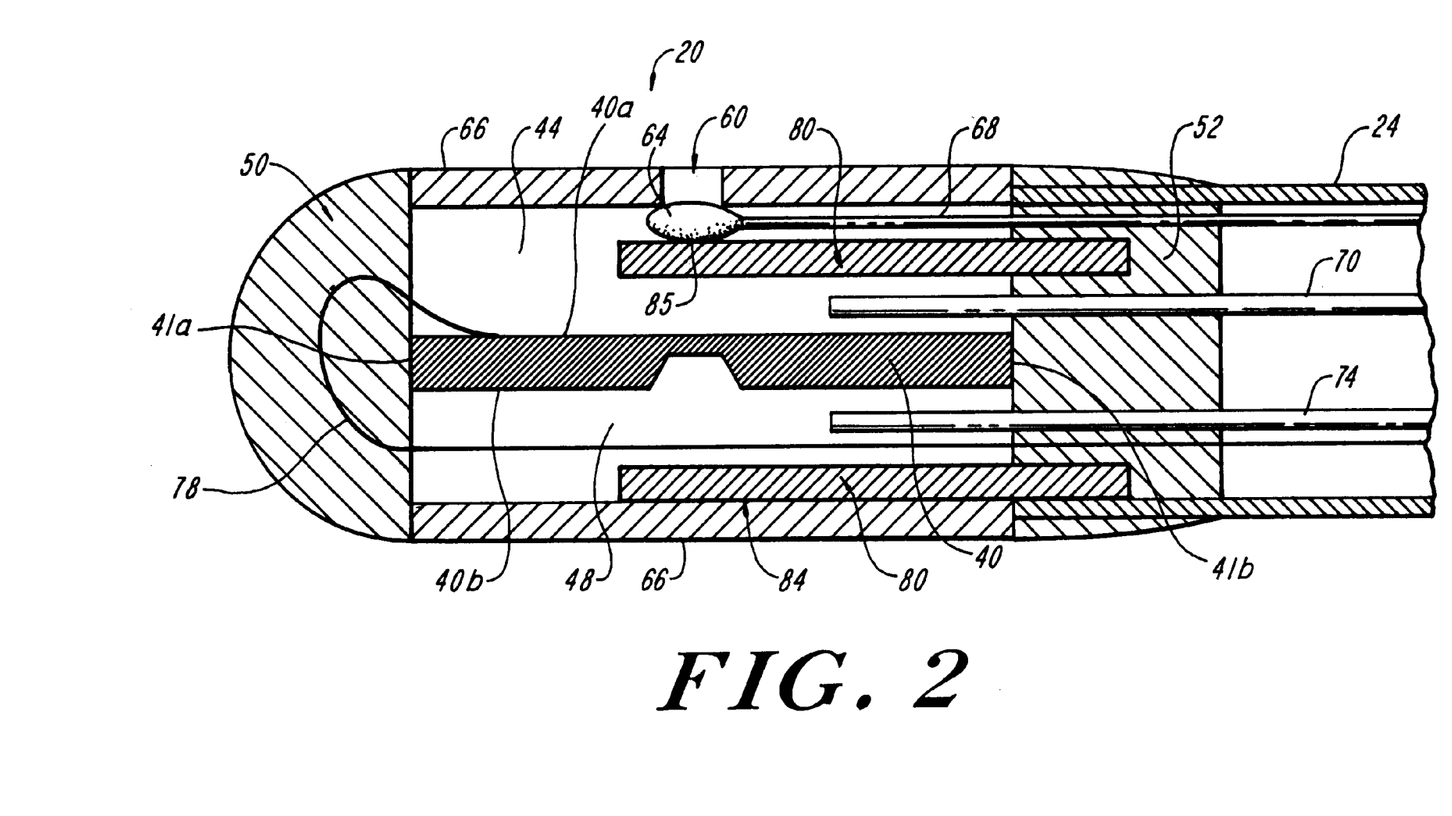
FIG. 2 is a cross-sectional view of the pressure sensing device of the invention mounted on the distal end of the catheter of FIG. 1.
Figure 2A:
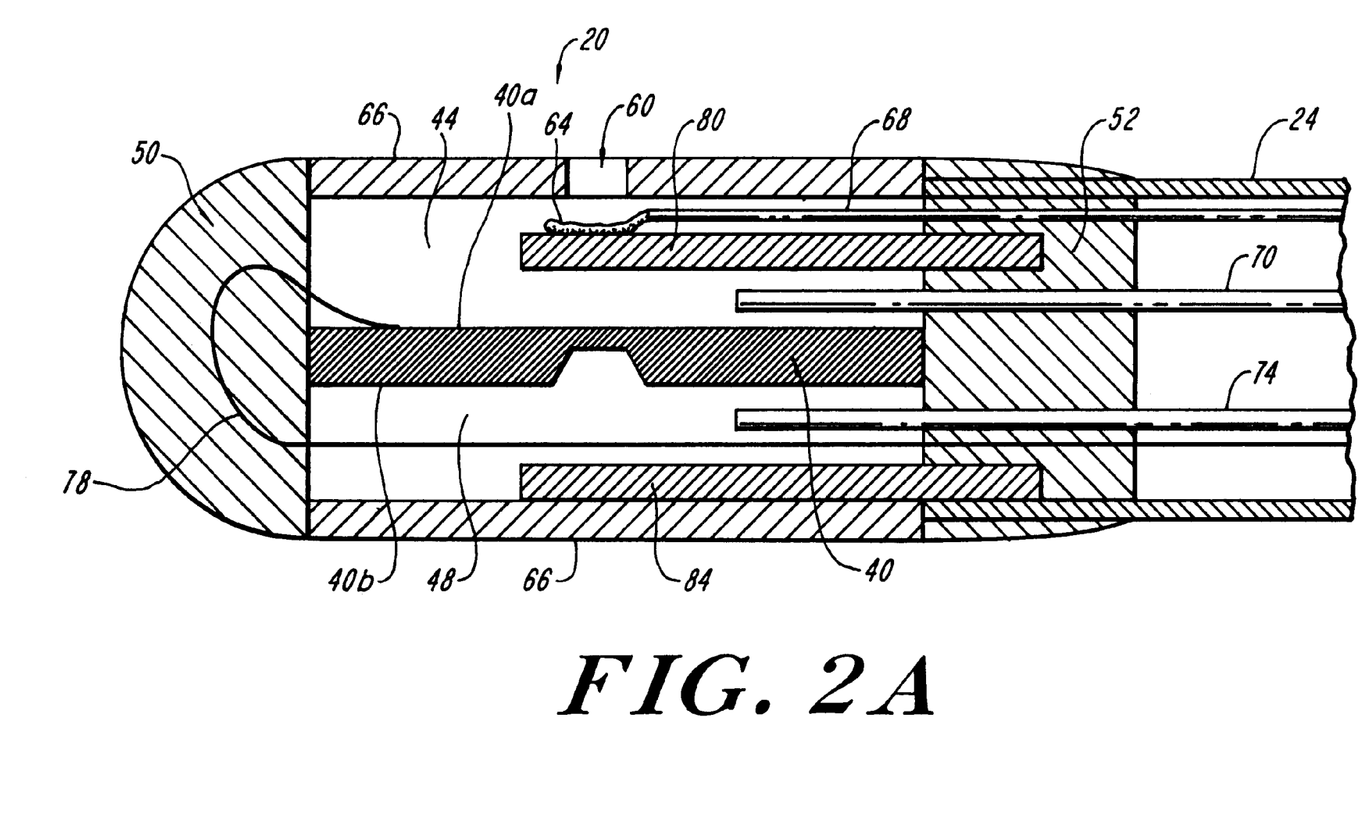
FIG. 2A is a cross-sectional view of the pressure sensing device illustrated in FIG. 2, showing a blocking element of the device in a deflated condition.

Referring also to FIGS. 2 and 2A, the pressure sensor tip region 20 at the distal end 16 of the catheter 10 is shown in cross-section to include a pressure sensor element 40. In the illustrative embodiment, the pressure sensor element 40 is a semiconductor device. The semiconductor can be a resistor network micromachined to be responsive to pressure applied to the chip surfaces. More specifically, pressure applied to the resistor network causes a change in resistance of the resistor network. It is understood that other suitable pressure sensor elements can be used providing that they can be isolated with the surfaces exposed to a common pressure.

The tip region 20 includes a first chamber 44 adapted for being exposed to the physiological pressure to be measured and a second chamber 48 adapted for being exposed to a reference pressure. During in vivo calibration, however, both chambers 44 and 48 are exposed to a reference pressure, as will be described.

The pressure sensor element 40 separates and isolates the first and second chambers 44,48. The pressure sensor element 40 is mounted in the tip region 20 so that the first chamber 44 is disposed adjacent to one surface 40a of the sensor element 40 and the second chamber 48 is disposed adjacent to an opposite surface 40b of the sensor element 40, as shown. The pressure sensor element 40 extends along its length between a terminal portion 50 of the tip region 20 and a barrier portion 52. Ends 41a,b of the pressure sensor element 40 are bonded to the terminal and barrier portions 50,52 with an adhesive. The adhesive provides a respective seal between along the ends 41a,b of the pressure sensor element 40 and the respective terminal and barrier portions 50,52.

The pressure sensor 40 also extends across the diameter of tube 66. The pressure sensor element 40 is mounted within the tube 66 and edges of the pressure sensor element 40 are bonded to walls of the tube. The adhesive extends along the edges of the pressure sensor element 40 to form a seal between the tube 66 and the pressure sensor element edges. Thus, the pressure sensor element 40 is bonded about its perimeter with an adhesive that provides a seal to effectively isolate the first and second chambers 44,48.

The first and second chambers 44 and 48 are isolated from one another but need not be of equal size. For example, the pressure sensor 40 can be positioned within the tube 66 so as to form two chambers of unequal size.

The adhesive used to bond the pressure sensor element 40 can be selected from suitable non-conductive, biocompatible, medical grade adhesives, such as epoxies and silicone adhesives.

In the illustrative embodiment, the barrier portion 52 is comprised of silicone or medical grade adhesive described above, such as an epoxy, that secures the tube 66 to the tube 24. The terminal portion 50 is formed from silicone, for example, secured to an end of the catheter tube 66.

As shown in FIGS. 2 and 2A, the catheter tube 24 abuts the tube 66. However, in another embodiment the catheter tube 24 may have an outer diameter smaller than an inner diameter of the tube 66 such that the catheter tube 24 can be inserted within the tube 66. The tubes 24, 66 can be bonded with an adhesive or by other means. Further, the diameter and wall thickness of the tubes 24, 66 can vary significantly without departing from the intended scope of the invention.

The tip region 20 includes an aperture 60 extending through a wall of the tube 66 to selectively expose the first chamber 44 to a physiological pressure external to the catheter 10. More particularly, in accordance with the invention, a blocking element 64 is provided for selectively blocking the aperture 60, as will be described. Physiological pressure measurements are made when the aperture 60 is unblocked and the pressure sensor 40 is calibrated, or zeroed, when the aperture 60 is blocked. In the illustrative embodiment, the tube 66 is comprised of titanium. However, other biocompatible materials that are non-magnetic and thus unaffected by a Magnetic Resonance Imaging (MRI) examination, such as stainless steel and titanium alloys, are also suitable.

In the illustrative embodiment, the blocking element 64 is a balloon which is adapted for being manipulated between a first, inflated condition in which the balloon blocks the aperture 60 (FIG. 2) and a second, deflated position in which the aperture is open (FIG. 2A). It is understood that a variety of other devices and/or mechanisms, other than a balloon may be used to block the aperture. For example, a membrane can be used to selectively occlude the aperture.

To inflate the balloon 64, a cylindrical member 68 extends between the balloon 64 and the proximal end 14 or respective coupling 36, 38 of the catheter via the passageway beginning at the tube 24 (FIG. 1). The cylindrical member 68 carries a gas or a fluid to and from the balloon 64 for inflating and deflating the balloon. Cylindrical member 68 can be connected to a syringe, or other air supply, via a luer connector for example, to inflate the balloon. The syringe may be removed to deflate the balloon.

A first cylindrical member 70 extends from the first chamber 44 through the tube 24 to the proximal end 14. The cylindrical member 70 is hollow and is adapted for carrying a gas to the first chamber 44 in order to calibrate the pressure sensor 40. More specifically, the gas directed into the first chamber 44 by the cylindrical member 70 is at the same pressure as a gas presented to the second chamber 48 during calibration. To this end, a second cylindrical member 74 extends between the second chamber 48 and the proximal end 14 of the catheter through the tube 24. The second cylindrical member 74 is adapted to carry gas at a reference pressure to the second chamber during calibration and during physiological pressure measurements.

In an exemplary embodiment, the second cylindrical member 74 is kept open to consistently expose one surface 40b of the pressure sensor element to atmospheric pressure. Thus, air at atmospheric pressure is present in the second chamber 48 during calibration and during pressure measurements. The first cylindrical member 70 is closed while physiological pressure measurements are made. This allows external pressure to be presented to the other surface 40a of the pressure sensor element. During calibration, however, the first cylindrical member 70 is opened to expose the other surface 40a of the pressure sensor element to atmospheric pressure. Thus, during calibration, both surfaces 40a,b of the pressure sensor element are exposed to atmospheric pressure.

In an alternative embodiment, the pressurized fluid source 35 (FIG. 1) provides gas to the first and second chambers 44,48 at a predetermined pressure during calibration. The pressurized fluid source 35 is selectively coupled to both the first and second cylindrical members 70,74. The pressurized gas ensures that the same pressure is present at both surfaces 40a,b of the pressure sensor element to more accurately zero the pressure sensor. The pressurized gas, such as air, overcomes any pressure differentials that can be caused by residual fluid in a chamber 44,48, from a physiological pressure measurement for example. Also, for atmospheric pressure, small differences in pressure can exist between the first and second chambers 44,48 due to the relatively long path from the connector 31 to the tip region 20. The pressurized gas provides a substantially equalized pressure distribution in the first and second chambers 44,48 for accurate calibration.

A cylindrical member 80 is mounted in the silicon barrier region 52 between the balloon 64 and the first surface 40a of the pressure sensor 40. As is apparent from FIG. 2, the cylindrical member 80 surrounds a portion of the pressure sensor element 40. A portion 85 of the cylindrical member 80 provides a backing plate when the balloon 64 is inflated to prevent the balloon from contacting and/or otherwise affecting the accuracy of measurements made by the pressure sensor 40. That is, the backing plate prevents any strain from being exerted by the blocking element 64 on the first side 40a of the pressure sensor 40.

Although the cylindrical member 80 provides a backing plate for the blocking element 64, the cylindrical member 80 cannot mechanically interfere with the mounting of the pressure sensor element 40 in the tube 66. More specifically, edges of the pressure sensor element 40 must extend across the diameter of the tube. To this end, the cylindrical member 80 includes at least one gap, groove, or other such opening that allows the pressure sensor element 40 to extend to the walls of the tube 66. It is understood that the cylindrical member 80 can have many configurations that provide the backing plate function for the blocking element 64 without preventing the pressure sensor element 40 from extending to the walls of the tube 66. For example, the cylindrical member 80 may only be present in the first chamber 44 where the blocking element 64 is located.

In addition to providing a backing plate for the blocking element 64, the cylindrical member 80 can provide further structural rigidity to the tip region 20 of the catheter. For example, a portion 84 of the cylindrical member can be affixed to the tube 66 by bonding with an adhesive, by ultrasonic welding or by other means.

An electrical conductor 78 is coupled between the pressure sensor element 40 and the connector 31 (FIG. 1) for electrical connection to the pressure monitoring circuit 33. The electrical conductor 78 carries an electrical output signal of the pressure sensor 40 indicative of a measurement of the difference in pressures presented to the first and second sides 40a, 40b of the pressure sensor 40. The pressure sensor 40 and pressure monitoring circuit 33 thus provide electronics for measuring a physiological pressure. Cylindrical members 68, 70 and 74 as well as electrical conductor 78 extend through the barrier region 52 into the tube 24. With this arrangement, the tip region 20, and in particular the first chamber 44 and the second chamber 48, remain isolated from the environment within the tube 24.

In an exemplary embodiment, the catheter tip region 20 has a diameter in the range of about one quarter to five millimeters, and preferably about two millimeters. The length of the tip region 20 can range from about one to ten millimeters, is typically between three and five millimeters, and most preferably is about four millimeters.

In operation, physiological pressure is measured when the balloon 64 is deflated as shown in FIG. 2A. In this condition, the first chamber 44 is in fluid communication with the exterior of the catheter via the unblocked aperture 60. Thus, the physiological pressure at the site at which the catheter is disposed is communicated to the first chamber 44. At the same time, a reference pressure is presented to the second chamber 48 via the cylindrical member 74.

The electrical output signal of the pressure sensor 40 carried by conductor 78 is indicative of the pressure differential between the first chamber 44 and the second chamber 48. Thus, where the physiological pressure is equal to the reference pressure, an output signal carried by the electrical conductor 78 is null. The output signal carried by conductor 78 is processed by the pressure monitor circuit 33. In the illustrative embodiment, the pressure monitor circuit 33 includes a Wheatstone bridge measurement circuit. The bridge circuit matches two resistances that correspond to the surfaces 40a,b of the pressure sensor element 40 with two resistors in the pressure monitoring circuit. The bridge circuit provides an output that is proportional to the amount of mismatch between resistors caused by the output signal. The resistance mismatch can be the result of pressure applied to the pressure sensor element or a drift in resistance not attributable to pressure. For a drift in resistance, the sensor should be zeroed to compensate for the drift. The pressure monitoring circuit can compensate for the drift in resistance with an interface element or with a device in the pressure monitoring circuit that stores and subtracts drift measurements. The pressure monitoring unit can include a display, such as a liquid crystal display (LCD), alarms, and peak positive and negative signal detection circuits.

Figure 3:
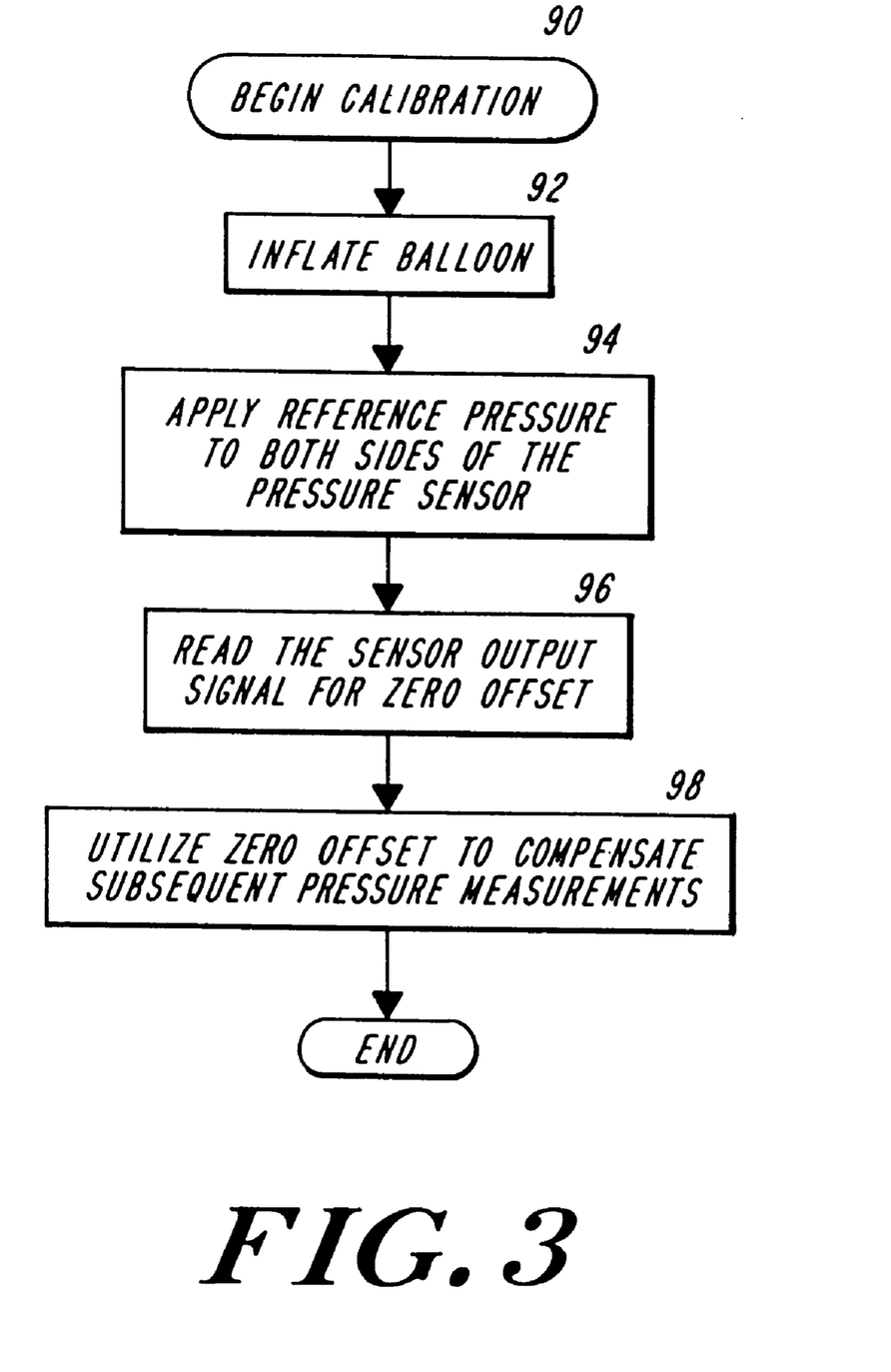
FIG. 3 is a flow diagram illustrating a process for in vivo zeroing of the pressure sensing device of FIG. 2.

Referring to FIG. 3, one illustrative process by which the pressure sensor of the present invention is calibrated in vivo is shown. It will be appreciated by those of ordinary skill in the art that the particular steps and sequence of steps is illustrative only and may be varied without departing from the spirit of the invention. Calibration of the pressure sensor 40 can be initiated, in step 90, either manually by a user at desired time intervals or, alternatively, automatically, such as at predetermined time intervals, under the control of the pressure monitoring circuit 33. To begin calibration of the catheter, the balloon 64 is inflated in step 92 to the position shown in FIG. 2 such that it blocks aperture 60. In this condition, the first chamber 44 is isolated from the physiological pressure exterior to the catheter 10. In step 94, a reference pressure, such as atmospheric pressure, is introduced through cylindrical member 70 into the first chamber 44 and through cylindrical member 74 into the second chamber 48.

The output signal 78 of the pressure sensor 40 is then measured by the pressure monitoring circuit 33 to determine the zero offset of the pressure sensor in step 96. Finally, in step 98, the measured zero offset is used by the pressure monitoring circuit 33 to compensate for the zero offset and to thereby enhance the accuracy of subsequent pressure measurements. In one embodiment, a Wheatstone bridge circuit is used to detect resistance changes. The two resistance values from the respective surfaces of the pressure sensor element are matched with two resistors in the pressure monitoring circuit 33 to form the bridge circuit. As resistances change due to pressure applied to one or more surfaces of the pressure sensor element or resistances drift, the bridge circuit provides an output signal proportional to the resistance mismatch in the bridge. In this way, the pressure at the sensor element can be measured. For resistance drift, a circuit element in the pressure monitoring circuit can compensate for the resistance mismatch in the bridge circuit to zero the pressure sensor. In another embodiment, the pressure circuit includes a circuit to store and subtract resistance drift.

Figure 4:
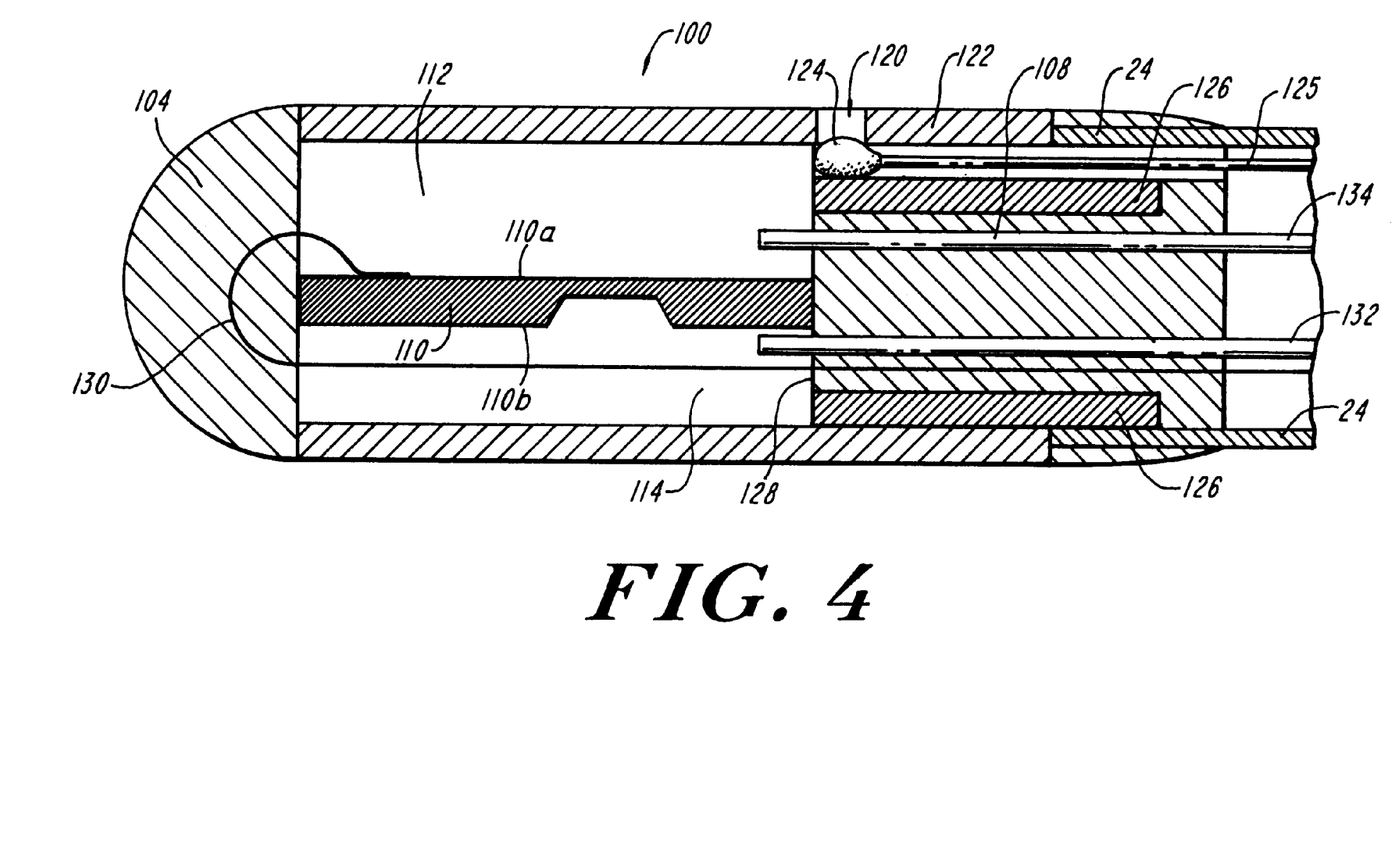
FIG. 4 is a cross-sectional view of an alternate embodiment of the pressure sensing device of the invention mounted on the distal end of the catheter of FIG. 1.

Referring to FIG. 4, there is shown an alternate embodiment of a tip region 100 comprising a pressure sensor permitting in vivo zeroing in accordance with the invention. The tip region 100 is suitable for use with the catheter 10 of FIG. 1. Like the catheter tip region 20 of FIGS. 2 and 2A, the tip region 100 includes a terminal region 104 and a barrier region 108 between which a pressure sensor element 110, such as a semiconductor element, is mounted. The pressure sensor 110 effectively divides the tip region 100 into two isolated chambers: a first chamber 112 adjacent to a first side 110a of the sensor and a second chamber 114 adjacent to a second side 110b of the sensor. The first chamber 112 is bounded by a portion of the tip region wall or tube 122, the terminal region 104, the first sensor surface 110a and the barrier region 108 and the second chamber 114 is bounded by a portion of the tube 122, the terminal portion 104, the second sensor surface 110b and the barrier region 108, as shown. The pressure sensor 110 is adhesively bonded to the tube 122 and the terminal and barrier portions 104, 108. The adhesive provides a seal to isolate the first and second chambers 112, 114.

An aperture 120 extends through the tube 122 in order to permit fluid communication between the first chamber 112 and the external environment during physiological pressure measurements. The aperture 120 is selectively blocked by a blocking element 124, such as a balloon 124, during in vivo calibration. To this end, a tube 125 is coupled between the balloon 124 and the catheter tube 24 by which fluid is introduced into the balloon to inflate it in response to user or automatic initiation of sensor calibration.

Figure 4A:
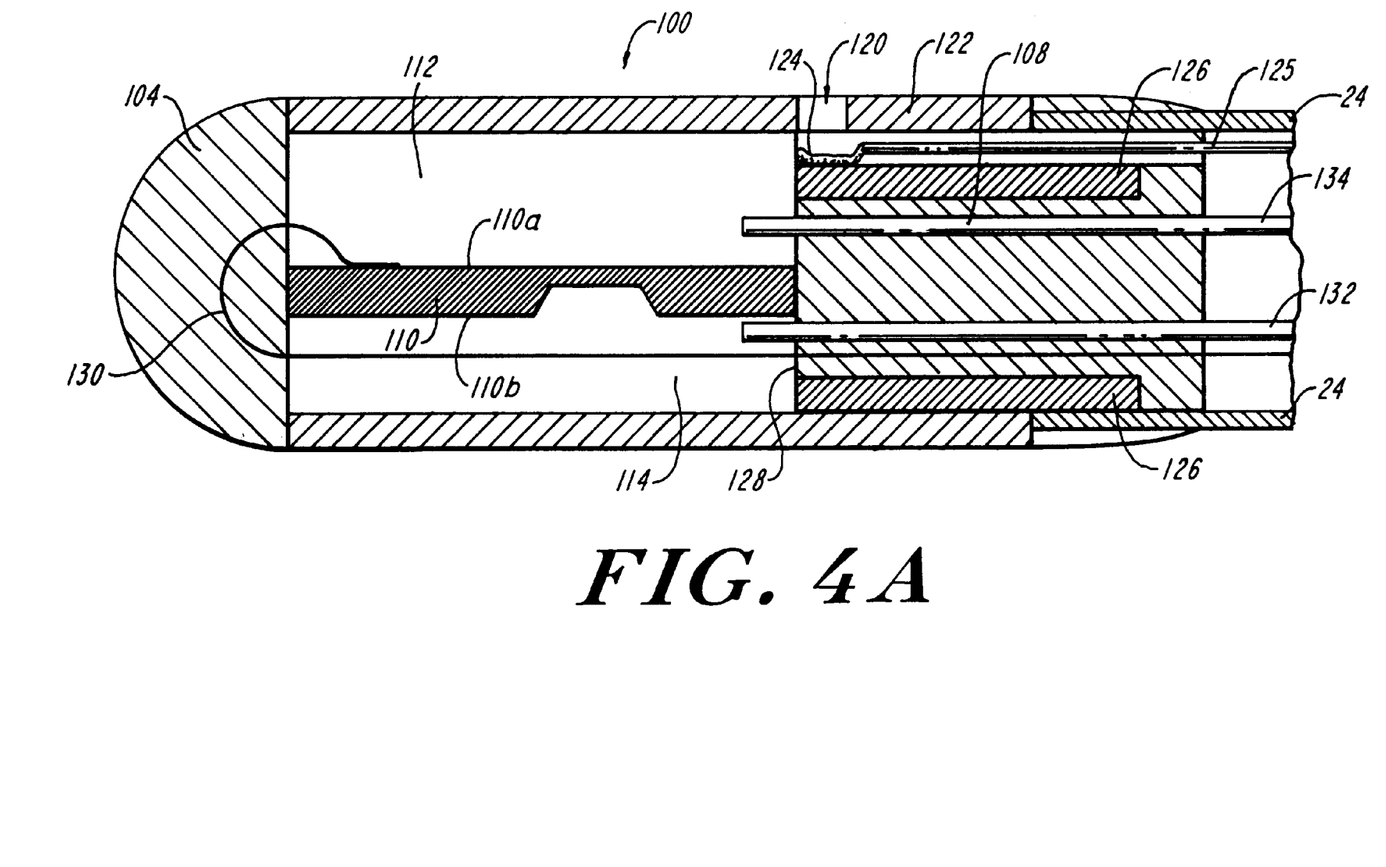
FIG. 4A is a cross sectional view of the pressure sensing device illustrated in FIG. 4, showing a blocking element of the device in a deflated condition.

A physiological pressure is measured while the balloon 124 is in the deflated condition, as shown in FIG. 4A, to expose the first side 110a of the pressure sensor element 110 to the physiological pressure at the site at which the catheter is disposed. A reference pressure is presented to the second side 110b of the pressure sensor element via tube 132 so that a differential pressure between the first and second sides of the pressure sensor element 110 can be measured. The pressure sensor element 110 provides an output signal indicative of the pressure differential between the first and second chambers 112,114. The output signal is carried by conductor 130 to a pressure monitoring circuit, like that shown and described in conjunction with FIG. 2.

When in vivo zeroing is desired, the balloon 124 is inflated to block the aperture 120 and seal the first chamber 112. A reference pressure is presented to the first chamber 112 via tube 134 and to the second chamber 114 via tube 132 so that there is no pressure differential between the first and second sides 110a, 110b of the pressure sensor element. An output signal indicative of this zero offset condition is provided to the pressure monitoring circuit via the conductor 130.

An optional cylindrical member 126 is embedded in the barrier region 108 to provide a backing plate for the balloon 124 and increase structural stability for the tip region 100 and barrier region 108 junction. The cylindrical member 126 does not extend into the first and second chambers 112, 114, but, rather, terminates at a wall 128 of the barrier region 108. As compared with the embodiment of FIG. 2, the tip region 100 is increased in length due to the placement of the aperture 120 with respect to the pressure sensor element 110, but has a similar diameter. The cylindrical member 126 can be a tube and will not interfere with the mounting of the pressure sensor element 110 in the tube 122, as in FIG. 2. If the cylindrical member is not present, a portion of the barrier region 108 proximate the aperture provides the backing plate function for the balloon.

The foregoing description of the illustrative embodiments of the invention is presented to indicate the range of constructions to which the invention applies. Variations in the physical architecture and dimensions of the invention will be apparent to those having ordinary skill in the art based upon the disclosure herein, and such variations are considered to be within the scope of the invention in which patent rights are asserted, as set forth in the claims appended hereto. All publications and references cited herein are expressly incorporated herein by reference in their entirety.

What is claimed is:

1. A physiological pressure sensing device, comprising:
   a pressure sensor tip having an external wall and an aperture disposed in the external wall;
   a pressure sensor element disposed within the pressure sensor tip and having a first surface exposed to the aperture and a second surface isolated from the aperture; and
   a blocking element adapted for movement between a first position in which the aperture is exposed and a second position in which the aperture is blocked.

2. The device of claim 1 further comprising electronics for measuring a physiological pressure when the blocking element is in the first position and for calibrating the device when the blocking element is in the second position.

3. The device of claim 1 wherein the pressure sensor tip is disposed at the distal tip of an elongate catheter.

4. The device of claim 1 wherein the blocking element is a balloon which is inflated when the blocking element is in the second position.

5. The device of claim 3 wherein the blocking element comprises a balloon, the device further including a calibration control disposed at a proximal end of the catheter and coupled to the balloon, which is inflatable upon actuation of the calibration control.

6. The device of claim 5 further comprising a backing plate disposed between the aperture and the pressure sensor element, the backing plate being effective to prevent strain on the pressure sensor element caused by the balloon.

7. The device of claim 3 further comprising a lumen extending from the pressure sensor tip to a proximal end of the catheter.

8. The device of claim 7 wherein a first cylindrical member disposed in the lumen extends into the pressure sensor tip adjacent to the first surface of the pressure sensor element and a second cylindrical member disposed in the lumen extends into the pressure sensor tip adjacent to the second surface of the pressure sensor element.

9. The device of claim 1 wherein the pressure sensor tip comprises a first chamber adjacent to the first surface of the pressure sensor element and a second chamber adjacent to the second surface of the pressure sensor element, wherein the first and second regions are isolated from one another by a barrier material.

10. The device of claim 1 wherein the pressure sensor element comprises a semi-conductor device.

11. The device of claim 8 wherein a third cylindrical member disposed in the lumen extends to the blocking element to move the blocking element between the first and second positions.

* * * * *